(12) United States Patent
Borich et al.

(10) Patent No.: US 7,803,322 B2
(45) Date of Patent: Sep. 28, 2010

(54) UNIVERSAL OPTICAL IMAGING AND PROCESSING SYSTEM

(75) Inventors: Damon Vincent Borich, Austin, TX (US); Steve Savoy, Austin, TX (US); Michael McAleer, Austin, TX (US); Andrew Milder, Austin, TX (US); Daniel Mitchell, Austin, TX (US)

(73) Assignee: Detekt Biomedical, L.L.C., Austin, TX (US)

( * ) Notice: Subject to any disclaimer, the term of this patent is extended or adjusted under 35 U.S.C. 154(b) by 1516 days.

(21) Appl. No.: 11/127,717

(22) Filed: May 12, 2005

(65) Prior Publication Data

US 2005/0201898 A1   Sep. 15, 2005

Related U.S. Application Data

(63) Continuation-in-part of application No. 10/640,134, filed on Aug. 13, 2003, now Pat. No. 7,267,799.

(60) Provisional application No. 60/403,238, filed on Aug. 14, 2002, provisional application No. 60/586,178, filed on Jul. 9, 2004.

(51) Int. Cl.
   *G01N 33/00* (2006.01)
   *G01N 21/00* (2006.01)

(52) U.S. Cl. .................. 422/68.1; 422/82.05; 422/62

(58) Field of Classification Search ............ 422/68.1, 422/82.05, 62
See application file for complete search history.

(56) References Cited

U.S. PATENT DOCUMENTS

| | | | |
|---|---|---|---|
| 5,580,794 A | 12/1996 | Allen | |
| 5,594,808 A | 1/1997 | Shen et al. | |
| 6,184,040 B1 * | 2/2001 | Polizzotto et al. | 436/43 |
| 6,394,952 B1 * | 5/2002 | Anderson et al. | 600/300 |
| 6,432,720 B2 | 8/2002 | Chow | |
| 6,495,373 B1 * | 12/2002 | Mauchan | 436/165 |
| 6,544,475 B1 | 4/2003 | Douglas et al. | |
| 6,563,653 B2 | 5/2003 | Ramm et al. | |
| 6,565,808 B2 | 5/2003 | Hudak et al. | |
| 6,567,163 B1 | 5/2003 | Sandstrom | |
| 6,576,476 B1 | 6/2003 | Taylor et al. | |
| 6,586,257 B1 | 7/2003 | Vuong | |
| 6,597,450 B1 | 7/2003 | Andrews et al. | |

(Continued)

OTHER PUBLICATIONS

U.S. Appl. No. 10/640,134, filed Aug. 13, 2003, Coffey, et al.

*Primary Examiner*—Lore Jarrett
(74) *Attorney, Agent, or Firm*—Toler Law Group

(57) ABSTRACT

The disclosure is directed to a test media reader module including a housing, a membrane, and an optical imager. The housing is configured to receive a test media adapter and has a barrier wall configured to separate the test media adapter from an interior of the housing. The barrier wall includes a window having an interior side and an exterior side. The membrane is transparent to a wavelength useful for imaging test media in the test media adapter. The membrane has a reactive region and overlies at least a portion of the exterior side of the window. The optical imager is located interior to the housing and is configured to image the test media located on the exterior side of the window along an optical path extending through the window and the membrane.

17 Claims, 5 Drawing Sheets

U.S. PATENT DOCUMENTS

| | | |
|---|---|---|
| 2001/0034068 A1 | 10/2001 | Spivey et al. |
| 2002/0060247 A1 | 5/2002 | Krishnaswamy et al. |
| 2002/0188224 A1* | 12/2002 | Roe et al. .................. 600/584 |
| 2003/0027244 A1 | 2/2003 | Colston et al. |
| 2003/0060682 A1* | 3/2003 | Handa et al. ............... 600/178 |
| 2003/0073931 A1 | 4/2003 | Boecker et al. |
| 2003/0112432 A1 | 6/2003 | Yguerabide et al. |
| 2003/0119202 A1 | 6/2003 | Kaylor et al. |
| 2003/0124738 A1 | 7/2003 | Crosby |
| 2003/0144582 A1* | 7/2003 | Cohen et al. ................ 600/316 |
| 2003/0214655 A1* | 11/2003 | Weiss et al. ................. 356/402 |
| 2005/0095697 A1* | 5/2005 | Bachur et al. ............ 435/287.2 |

* cited by examiner

UNIVERSAL OPTICAL IMAGING AND PROCESSING SYSTEM

CROSS-REFERENCE TO RELATED APPLICATION(S)

The present application claims priority from U.S. patent application Ser. No. 10/640,134, filed Aug. 13, 2003, entitled "Universal Optical Imaging and Processing System," naming inventors Damon Vincent Borich and William Patrick Coffey, and claiming priority from U.S. Provisional Patent Application No. 60/403,238, filed Aug. 14, 2002, entitled "Universal chemical and biochemical optical imaging and processing system," naming inventors Damon Vincent Borich and William Patrick Coffey, each of which applications is incorporated by reference herein in its entirety.

The present application claims priority from U.S. Provisional Patent Application No. 60/586,178, filed Jul. 9, 2004, entitled "RFID Booster Board Configurations," naming inventors Damon Vincent Borich, Steve Savoy, Andrew Milder, Dan Mitchell, and Michael McAleer, which application is incorporated by reference herein in its entirety.

FIELD OF THE DISCLOSURE

This disclosure relates generally to optical imaging and processing systems.

BACKGROUND

Numerous systems and instruments have been created to aid in the detection of analytes from a wide variety of mediums, such as solid, liquid, and gas mediums. Such systems and instruments have been created for use in, for example, the fields of medical diagnostics, air and water quality monitoring, food and beverage testing, and chemical and bio-threat detection. Typical systems and instruments range from hand-held portable devices, such as blood glucometers and portable biothreat detectors, to laboratory based instruments, such as spectrometers and automated clinical chemistry detectors. Despite this evolution in automated testing, these systems typically interface with a discrete or limited range of samples or sample cartridges and have limited cross-field diagnostic capabilities. Such limitations often result from systems using application specific diagnostic devices that lack hardware, software and processing flexibility to address new test architectures and protocols. As a result, the average consumer or industry technician is faced with a multitude of disparate limited devices with differing operation protocols.

Rapid diagnostic test strips and cartridges have been created to detect a broad range of chemical and biological agents. The majority of these tests quantify the presence of particular analytes by producing a color change or visible line or zone signifying the analytes presence or level. For test strips or cartridges capable of detecting multiple analytes, several potential lines or zones of color change may signify the presence of analytes. Test strips and cartridges are available for detection of many analytes ranging from drug metabolites, pregnancy hormones, anthrax, $E.\ Coli$, blood glucose, pH, and chlorine concentration. Typically, the physical embodiment of test media varies widely according to the application and the manufacturer. In some examples, the test media is the size and shape of a stick of gum, a business card, or a thin bookmarker. Generally, the test media have a region that is visible by the user for subjective interpretation of the test results.

Test media may be activated via a variety of test methods. Depending on a particular test and protocol employed, a user may dip the test strip into a fluid, apply fluid using a dropper, place the test strip on a fluid (e.g., blood drop on finger), or expose the strip to ambient conditions. Once the test media is activated and the sample is added, a set time is generally allowed to elapse, after which the user typically visually inspects the test media for color changes in the designated regions. These color changes are often compared to a reference that indicates threshold levels for quantified analyte levels.

As test media become available for an increasing number of analytes, related tests and analyte detection methods are used in an increasing number of in-field applications, such as environmental monitoring, criminal investigations, hazardous materials (HAZMAT) response, and biological and chemical terrorism investigation. Test media for one analyte may be influenced by ambient conditions and the presence of another analyte. As such, on-site investigators are increasingly measuring additional factors that may influence a test media and are under pressure to maintain an untainted chain of evidence.

Accordingly, there is a need for an improved test media processing system.

SUMMARY

In one particular embodiment, the disclosure is directed to a test media reader module including a housing, a membrane, and an optical imager. The housing is configured to receive a test media adapter and has a barrier wall configured to separate the test media adapter from an interior of the housing. The barrier wall includes a window having an interior side and an exterior side. The membrane is transparent to a wavelength useful for imaging test media in the test media adapter. The membrane has a reactive region and overlies at least a portion of the exterior side of the window. The optical imager is located interior to the housing and is configured to image the test media located on the exterior side of the window along an optical path extending through the window and the membrane.

In another embodiment, the disclosure is directed to an analysis membrane including a transparent film that is transparent at a wavelength of electromagnetic radiation useful for analyzing a test media. The analysis membrane also includes a reactive zone disposed on or within a portion of the transparent film.

In a further embodiment, the disclosure is directed to a method of analyzing test media. The method includes imaging the test media through a reactive region of a membrane to produce an image. The reactive region is responsive to a proximate condition. The method further includes determining the proximate condition by evaluating the image and determining a test result indicated by the test media by evaluating the image.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DESCRIPTION OF THE DRAWING(S)

Figure 1:
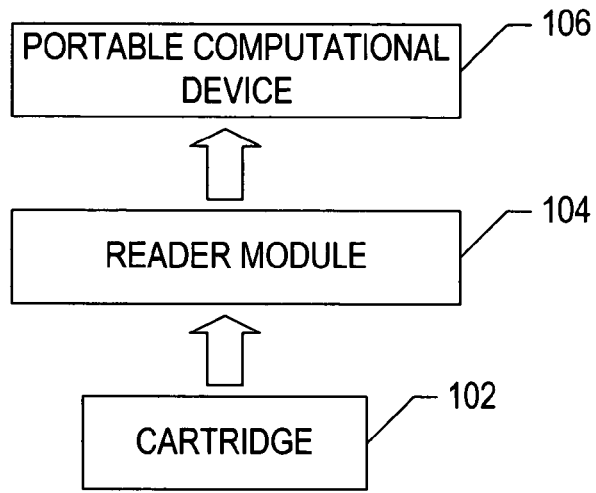
FIGS. 1, 2, and 3 include illustrations of exemplary test media reader modules.

In a particular embodiment, the disclosure is directed to a film or membrane that is optically transparent at a wavelength associated with analysis of an analytical test media. The film or membrane also includes a reactive region responsive to proximate conditions, such as temperature, humidity, and the presence of chemical or biological species. In one exemplary embodiment, the membrane is included in a stack of membranes that are adhered to one another using a releasable adhesive. The stack of membranes is configured to overlie an optical window of a test media reader such that the reactive region of the membranes is in an optical path of the test media reader. A top membrane of the stack may be removed to expose an underlying membrane. In response, an active region of the underlying membrane reacts to proximate conditions, resulting in a display readable by the test media reader.

The test media reader may include a physical barrier having a window having first and second sides. In one embodiment, the membrane is located on one side of the window and optical components configured to read test results through the window are located on an opposite side. In addition, the test media reader is configured to couple to a test media adapter. The test media adapter is configured to receive disposable test media, such as test strips, cartridges, or biochips, and, when coupled to the test media reader, locate active regions of the test strips or cartridges such that the optical components may image the active region of the test strips or cartridges through the window and optionally the membrane.

In a particular embodiment, prior to performing a test, a top film is removed to expose an underlying film having a reactive region. The reactive region of the underlying film reacts to proximate conditions, such as temperature, humidity, atmospheric gases, volatile chemicals emitted from the test strip or cartridge, and other ambient conditions. The optical component images both the reactive region of the membrane and the active region of the test strip or cartridge. In one embodiment, the reader analyzes the imaged data to determine test data. Alternatively, the image data may be provided to a general purpose handheld circuitry for further analysis and displayed to a user.

In a further exemplary embodiment, the reader may include an antenna for accessing radio frequency identifiers (RFID tags). When a cartridge including an RFID tag is located proximate to the antenna or when the cartridge is inserted into a cartridge adapter attached to the reader, the RFID antenna may access data stored on the cartridge. This data may, for example, indicate a unique identifier of the cartridge, an identifier associated with the cartridge type and information associated with reading of test results from the cartridge. In one particular embodiment, the reader images the cartridge to perform an analysis of a test performed by the cartridge and transmits test results associated with that analysis to the cartridge for storage.

In another embodiment, the reader system, including the reader module and attachable adapter housings, accepts a broad range of standard commercially available and custom lateral flow, dry chemistry test strips, and biochips through a standard mechanical interface via the adaptable cartridge housing or cartridge adapter. When determining test results, the reader performs optical interrogation of a cartridge, for example, by imaging the active region of the cartridge chemistry via a complimentary metal-oxide semiconductor (CMOS) or charge-coupled device (CCD) detector. Illumination may be provided by a series of optically tuned light emitting diodes. As a result, raw image data is collected, digitized, and stored in an on-board memory. This information may be processed using a host device's (e.g. PDA, laptop, cellular phone) processing capabilities in conjunction with the software component of the system. In one embodiment, software pre-loaded onto the reader or the host device provides the processing instructions and compares image analysis data to pre-defined calibration data, yielding a quantitative result. The reader may interface with the host device through several different physical standards. These standards include industry standards such as Personal Computer Memory Card International Association (PCMCIA), Universal Serial Bus (USB), Serial, Secure Digital, BlueTooth®, WiFi, Compact Flash or other company specific standards such as the Handspring Springboard Platform™.

In another embodiment, software provides for automated adaptable chemical and biochemical optical imaging for cross-field testing compatibility. For example, the software may be operable by a general purpose computational device, such as a PDA, laptop, personal computer, or cellular telephone, and may be stored on computer readable media, such as optical or magnetic media, accessible for implementing the imaging analysis. The reader system, including the test media reader and the optional general purpose computational device, is intended to provide for analysis of a wide array of test media including standard commercial lateral flow strips, biochips, and/or disposable chemical and biochemical assays. The system digitizes and objectively quantifies results from test media (such as test strips that are conventionally read by a human visually); stores original images and data into memory for review; and enhances test processing by executing image processing algorithms.

FIG. 1 includes an illustration of an exemplary embodiment of an analysis system. FIG. 1 illustrates portable computational circuitry 106, such as a standard personal digital assistant (PDA) or multipurpose handheld circuitry, interfacing with an optical reader 104, which in turn accepts cartridges 102. The reader 104 interfaces with the PDA 106, for example, through a mechanical interface that provides structural support and houses electrical communication ports for the reader 104 and PDA 106. The exemplary embodiment allows the user to hold the instrument in one hand, insert a cartridge into one side of the reader using their other hand, and activate an automated software analysis routine.

The reader 104 may alternatively interface with electronic devices other than a PDA, including laptop and desktop computers, cellular phones, or other devices that have data input and display components. The interface with the PDA or other devices may be through standard communications ports, such as Personal Computer Memory Card International Association (PCMCIA), Universal Serial Bus (USB), FireWire, infrared, WiFi, Bluetooth®, Compact Flash or other custom communication protocols. The reader 104 may include electronic components, such as a Field Programmable Gate Array (FPGA) and/or a microcontroller that may be re-configured to utilize the appropriate communication protocol. Computer program logic to execute multiple protocols may be embedded in the reader 104 and the communication ports may be accessible using standard pre-installed electrical connectors. An exemplary reader module 104 is disclosed in U.S. patent application Ser. No. 10/640,134, incorporated herein by reference in its entirety.

Figure 2:
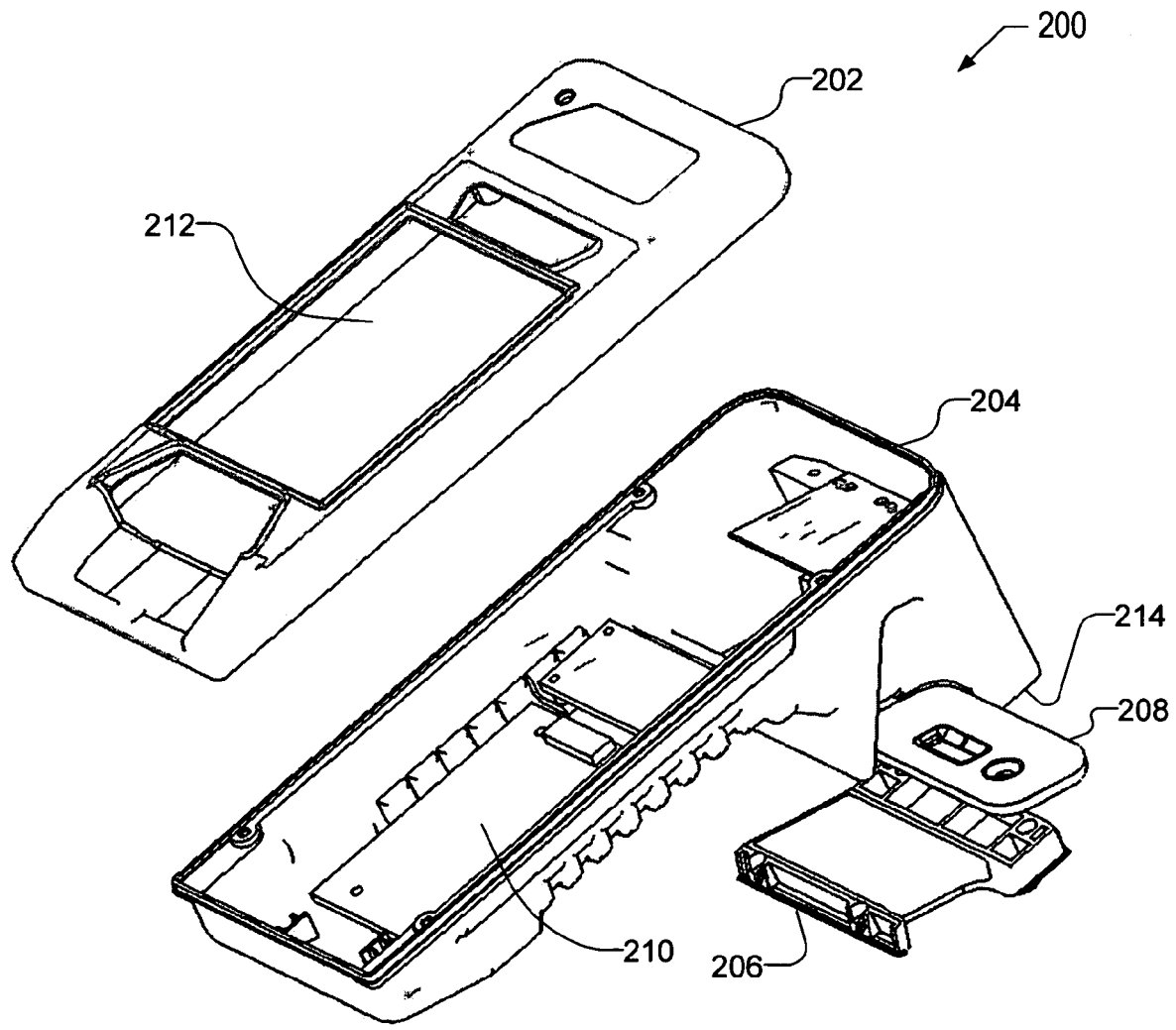

FIG. 2 includes an illustration of an exemplary reader module 200. The reader module 200 includes a top housing 202 configured to couple with a bottom housing 204. In one particular embodiment, the top housing 202 is configured to receive a portable handheld device, such as a personal digital assistant (PDA), and includes a window 212 through which an interface of the portable handheld device is accessible. The bottom housing 204 is adapted to hold reader components 210, such as microprocessors, a FPGA, and optical imaging components. The reader components 210 are configured to communicate with the handheld device.

The bottom housing 204 is also configured to detachably couple to a removable test media adapter 206. Internal optics and electronics cavities are typically sealed by a barrier separating disposable test media 208 and the test media adapter 206 from the internal reader components. The barrier (not shown) includes an opening with an optional optically transparent membrane or window to the cartridge region.

In alternative embodiments, the test media adapter 206 may be adapted to hold test strips of various sizes and types, cartridges of various sizes and types, or configured such that the reader can receive other analytical devices. In one exemplary embodiment, the test media adapter 206 is configured to detachably couple to a bottom 214 of the bottom housing 204. In a particular embodiment, the test media adapter 206 is an externally removable and re-configurable cartridge track adapter. Typically, test media adapters 206 may be removed, replaced and or exchanged by the end user without disassembly of the reader. In one example, the test media adapter 206 forms a base or resting surface of the reader module. In another example, the adapter 206 may be removed for cleaning in aqueous and non-aqueous sterilizing and disinfecting solutions and additionally may be submerged, while attached to the reader, to conduct aqueous testing. The removable adapter 206 may be pre-treated with surface coatings, growth mediums, protein, DNA adsorption media, and features to inhibit or accelerate bacterial, viral, fungal, and mold growth.

In another exemplary embodiment, the removable cartridge adapter 206 may be used to gather external cartridge contaminants, through frictional contact with the cartridge housing and a sample inlet port for further biological testing, such as culturing, polymerase chain reaction (PCR), Mass spectroscopy, infrared (IR) spectroscopy, and other general analytical chemistry techniques. In addition, the removable cartridge adapter 206 may allow multiple cartridges to be loaded simultaneously and may be manually or automatically rotated to expose individual cartridge test regions, such as up to ten unique test cartridges. In a further embodiment, the disposable cartridges may exhibit varying dimensions and configurations. The optical focal length may be maintained by varying the depth, thickness, and overall dimensions of the cartridge adapter 206. Alternatively, cartridges, such as glass microscope slides and "biochips," may be imaged through the window of the barrier.

In a particular embodiment, the removable cartridge adapter 206 is configured to hold the cartridge 208. In one example, the cartridge 208 is placed horizontally with the normal force of gravity perpendicular to the cartridge plane, discouraging fluid flow into the electronics cavity and promoting vapor and gas phase compounds to rise towards the optically transparent opening in the barrier. Typically, the cartridge 208 is configured to perform a test to detect a preselected type of analyte.

Figure 3:
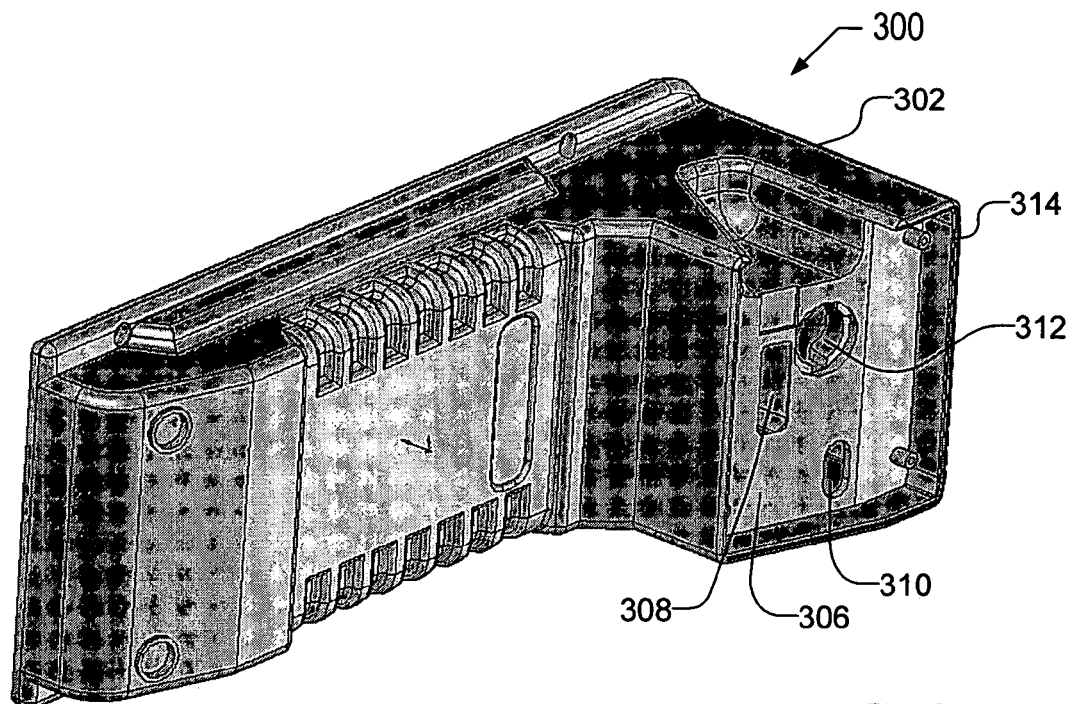

FIG. 3 includes an illustration of a bottom portion of an exemplary reader module 300. The reader module 300 includes a housing 302 and an underside region 314 that is configured to detachably couple to cartridge adapters. The underside region 314 also includes a barrier 306 separating the interior of the housing 302 and internal reader module components, such as optical imaging components, from the cartridge, cartridge adapter and ambient conditions. The barrier 306 may include a window 308 through which the optical components of the reader module 300 take images of active regions of cartridges and test strips. The window 308 may, for example, have an interior side on the interior of the housing 302 and an exterior side on the cartridge side of the barrier 306. The window 308 may be adapted to receive a single membrane or a stack of membranes on the exterior side that are optically transparent at a wavelength useful in analyzing the test media.

In one exemplary embodiment, the barrier 306 includes a recess 312 for receiving an antenna. For example, the antenna may be used to detect RFID information. The antenna may further provide radio frequency signals useful for retrieving RFID data from a test media and for providing test result data to the test media for storage in the test media, such as in a RFID tag. In another exemplary embodiment, the antenna may transmit electromagnetic radiation to transfer power to the cartridge. In one particular embodiment, the power is used to heat the cartridge or drive electronic or mechanical components of the cartridge. Alternatively, electronic identification badges having RFID tags or other optical signatures and having overall dimensions similar to the disposable test media may be imaged and electronically detected by the reader optics and electronics.

In a further exemplary embodiment, the barrier 306 may include a mounting element 310 for mounting other electronic hardware and testing equipment to the reader module 300. For example, the mounting element 310 may house a switch or lever, indicating proper loading of a cartridge, test strip or cartridge adapter. In another exemplary embodiment, the mounting element 310 may house sensors, such as electrochemical sensors, volatile organic sensors, radioactivity sensors, ambient condition sensors, electromagnetic sensors and chromatographic sensors.

In a particular embodiment, the reader module 300 is configured to receive a single membrane or a stack of membranes (not shown) that overlie the window 308 on an exposed side of the barrier 306. Such membranes may include a reactive region or regions adapted to respond to proximate conditions, such as those conditions within a headspace between a test media and the barrier 306. Generally, the reader module 300 includes optical circuitry configured to take images of the test media through the window 308 and membrane (not shown).

Figure 4:
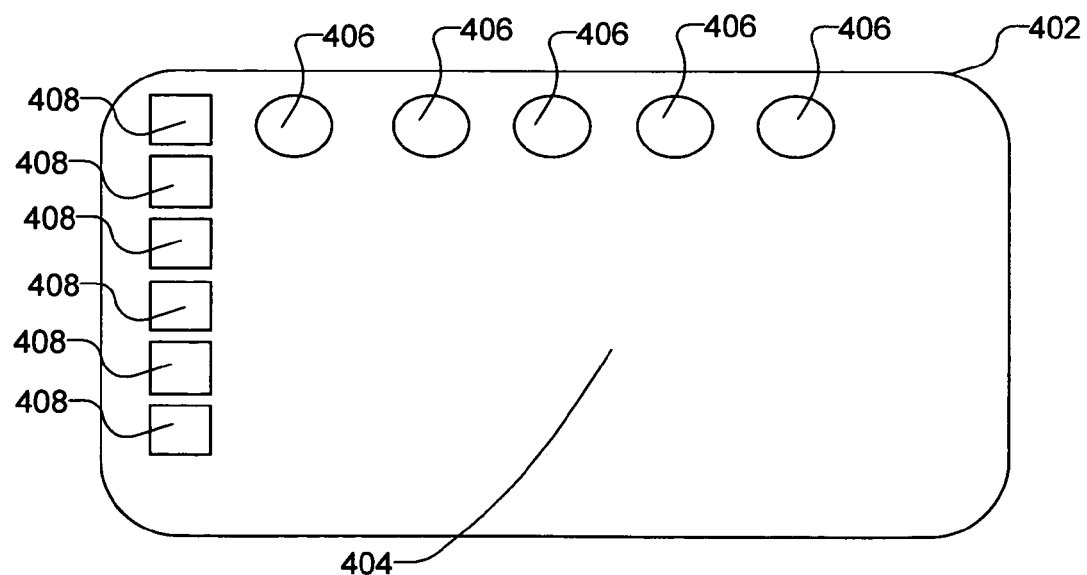
FIGS. 4 and 5 include illustrations of exemplary membranes for use with a test media reader module, such as the test media reader modules illustrated in FIGS. 1, 2, and 3.

FIG. 4 includes an illustration of an exemplary membrane or film 402 that may be disposed within the window 308. Typically, the membrane 402 is attached to a window of a barrier that separates a cartridge region and imaging optics. The membrane 402 includes a transparent region 404 transparent to a wavelength useful in analyzing test media, such as test strips or cartridges. In one exemplary embodiment, the transparent region 404 is transparent to visible wavelengths of light. In alternative embodiments, the transparent region may be transparent to infrared or ultraviolet (UV) regions of the electromagnetic spectrum. In one example, the membrane 402 may have optical filtering properties useful for enhancing images of test media. For example, the membrane 402 may have color additives or coatings to act as color filters, optical bandpass filters, tinting agents, polarization and contrast enhancing structures or optically tuning properties. In another example, the membrane 402 may enhance or enable fluorometric analysis by blocking wavelengths of light reflected from the cartridge region that are not significant to the test signal and by simultaneously allowing test signals of an appropriate wavelength or wavelength range to pass through to an imaging electronics cavity.

As illustrated, the membrane 402 also includes a reactive region, such as reactive regions 406 and 408. In a particular embodiment, the reactive regions (406 and 408) react to proximate conditions. In one example, the proximate conditions are ambient conditions under which the test or detection of analytes is performed. Such proximate conditions include temperature and humidity. In another example, the reactive regions may respond to proximate conditions, such as the presence of volatile chemicals associated with the test or cartridge, including volatile organic chemicals, or chemicals present in an ambient atmosphere. In a further exemplary embodiment, the cartridge 702 and or the test media adapter 710 may be replaced with a fan unit. The fan unit may direct ambient air, vapors, or aerosols from outside the reader over the membrane reactive regions, which may react with analytes in the air. In one embodiment, the membrane is sensitive to a gaseous and vapor phase compound, such as chlorine, cyanide, a combustible component, a nerve agent, or an oxidizer. For example, such analytes may include chemical or biological hazards, such as phi-x-174 bacterial phage, lewisite (L), distilled mustard (HD), sarin (GB), V-Agent (VX), hydrogen sulfide ($H_2S$), byproducts of nerve and blister agents, sulfur mustard, cyanogen chloride, hydrogen cyanide, and a variety of volatile organic compounds (VOC'c), such as acetone, acetonitrile, ethyl acetate, hexane, and tetrahydrofuran.

In general, the reactive regions of the membrane respond to the presence of analytes or to proximate conditions by providing optical indicators. As illustrated, the membrane may have multiple reaction regions (e.g., 406 and 408), partitions or quadrants exhibiting different optical characteristics and may have different chemical detection reaction zones and vapor collection regions for use in conjunction with image data to produce a multi-parameter analytical result. The response to ambient conditions may include a change in color, a change in light transmissivity, or a distortion of the membrane. In one example, the membrane may change optical character in the form of color changes, optical density changes, polarization changes, structural changes (e.g., wrinkling, warping, peeling) or pattern production (e.g., dots, streaks, bands, lines, character production ABCD etc.) upon reacting with a compound emanating from the test media, the test media fluid sample, or the air space above the test media. Generally, the reactive region of the membrane is located within an optical path of optical components of the reader module. As such, the optic components of the reader module can image the reactive regions of the membrane alone or when imaging test media. As a result, the optical changes are correspondingly detectable by the imaging components of the reader and appear as colorimetric alterations to raw pixel data collected from the reader's optical components (e.g., a complementary metal-oxide semiconductor (CMOS), a charge coupled device (CCD), a linear diode, etc.). The optical changes may be automatically recognized via algorithms or magnified and viewed by the user in the raw image when compared to an un-reacted image. As a result, handheld devices attached to the reader module or the reader module itself may analyze images of the membrane's reactive regions to determine the proximate conditions to which the membrane is exposed. The resulting data may be stored in the handheld circuitry, the reader module, or written to a test media, such as a cartridge.

In one exemplary embodiment, the membrane 402 includes a flexible substrate formed of a transparent material. Typically, the flexible substrate is a pressure sensitive adhesive coated polymer film, such as a polyester film, configured to cover the imaging window. Polyester films are available in a variety of thicknesses and custom sizes from commercial suppliers. In one particular embodiment, the flexible thin film substrate is coated with color changing reagents, enzymes or chemically responsive dyes that target common functional groups, chemical agents, and compounds. The membrane may be directly coated (e.g. via contact printing) or may have chemical reagent reservoirs, such as standard nitrocellulose pads adhered to the membrane surface.

In other embodiments, layers of the transparent film may sandwich chemical reservoirs or pads and may selectively control exposure and diffusion of gases into the reactive zone. By varying the composition and thickness of the polymer films, a range of porous translucent membranes can be constructed. In one embodiment, a thin layer of chemically reactive beads with individual diameters under 750 microns, formed, for example, of agarose and/or polyethylene glycol, polystyrene or other combinations and derivatives, are placed in between two layers of polyester film and provide a variety of chemical detection capabilities, while maintaining a transparent window in the unreacted state. In one example, the reactive region of the membrane 402 encompasses the entire surface of the membrane 402, remaining transparent when unreacted. In a particular embodiment, the membrane 402 is removed by the user after a given test period and analyzed using a multitude of secondary analytical tests, such as radioisotope emission, trace element analysis, chemical interrogation and associated tests.

Figure 5:
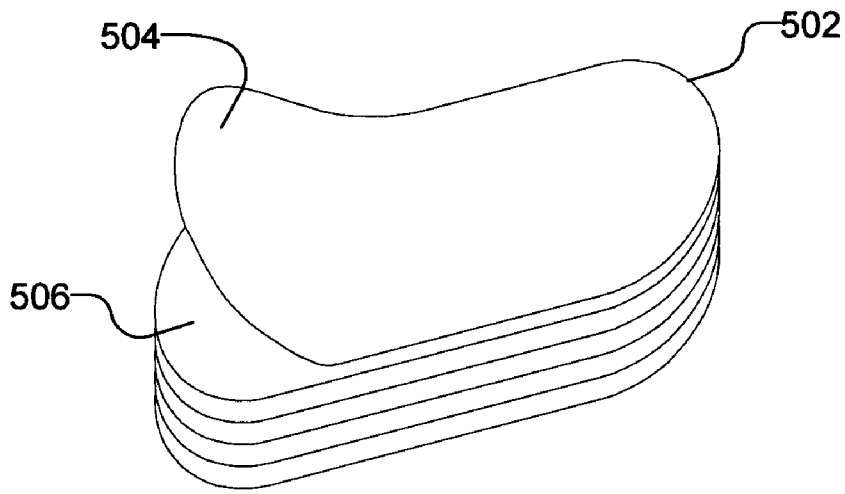

The membrane may be included in a stack of membranes, such as stack 502 illustrated in FIG. 5. When a top most membrane 504 is removed from the stack, an underlying membrane 506 is exposed to the proximate conditions. The stack 502 may be configured to overlie a window of a reader module such that reactive regions of the membranes can be imaged by optical circuitry of the reader module. In another example, the stack includes a top most protective film that prevents exposure of underlying membranes to ambient conditions prior to a first test. For example, when the stack 502 is inserted into a reader module, the protective film may be removed, exposing the first membrane. In addition to providing a reactive region, removal of subsequent membranes removes dust and oils from the optical path, providing a clear and unobstructed optical path for subsequent imaging and analysis. As such, a single or a multitude of removable membranes may be placed over the window and removed sequentially upon contamination, exposure, reaction or formation of an optical interference. Alternatively, membrane layers may be chemically degraded exposing other reactive layers or membranes.

Figure 6:
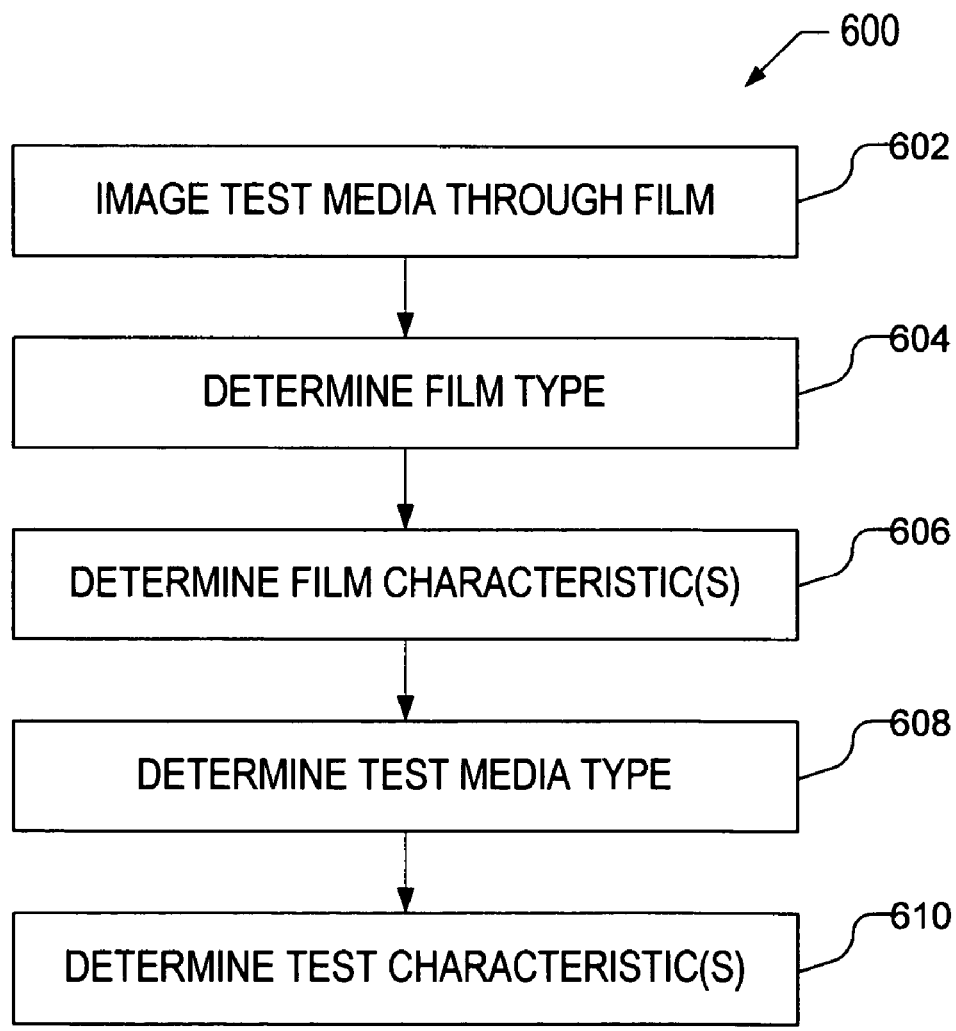
FIG. 6 includes an illustration of an exemplary method for detecting the presence of analytes.

FIG. 6 includes an illustration of an exemplary method 600 for performing an analysis of a test media, such as a test strip or cartridge. Further exemplary methods are disclosed in U.S. patent application Ser. No. 10/640,134, incorporated herein by reference in its entirety. For example, a top most membrane or film may be removed, exposing an underlying membrane or film to proximate conditions. An imager or optical component images a test media, such as a test strip or cartridge, through the film, as illustrated at 602. In one exemplary embodiment, the film includes an identifier region. In addition, a cartridge may include an identifier region or some readable identifier, such as an RFID tag.

The reader system may determine a film type using the film identifier, such as illustrated at 604. In one example, the reader system provides an interface to a user to request information about the film type. For example, the user may be prompted for entry of the film identifier via a PDA interface. In another example, the imager analyzes the identifier region of the film and determines a film type. In a particular embodiment, the identifier or film type may be used to reference a database of parameters that indicate how reactive regions of the film are to be imaged, interpreted and characterized. Using these parameters, the film characteristics may be determined, as illustrated at 606. For example, reactive regions may be analyzed for color changes, pattern changes, or changes in optical qualities, such as distortions. These pattern changes may be interpreted by the reader module or handheld device to identify proximate conditions.

The test media may also include an indicator, such as a color coding, bar code, or RFID tag that uniquely identifies the test media being imaged. Alternatively, the removable cartridge adapter may be optically and electronically encoded to indicate a cartridge type to the reader through use of image processing algorithms. In a particular embodiment, the test media type is determined, as illustrated at 608. For example, a database of test cartridges or test strips may be accessed to determine the type of test media and to determine parameters associated with imaging and interpreting the test media. Using these parameters, the test characteristics, such as results of an analysis or detection of an analyte, may be determined, as shown at 610. For example, images of the cartridge may be analyzed to determine the results of a test. Such analysis includes observing color changes, the location of lines, symbols, or absences thereof and determining the meaning of such observations.

Figure 7:
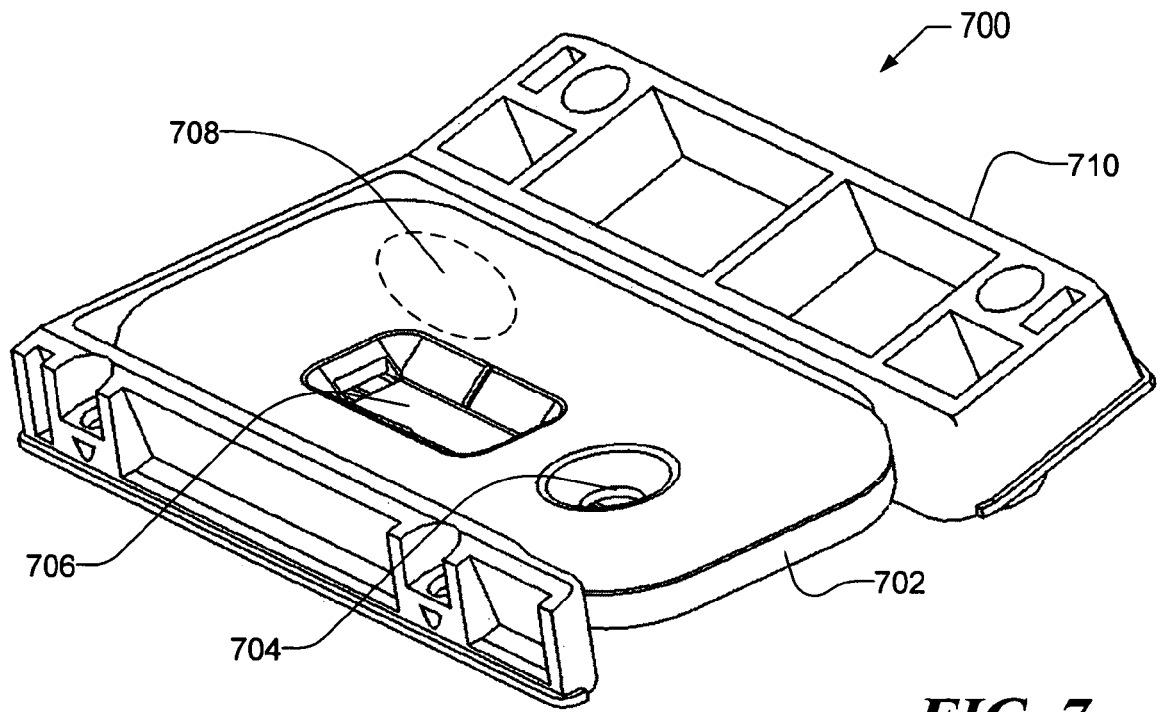
FIG. 7 includes an illustration of an exemplary test media and test media adapter.

In a particular embodiment, the test media is a cartridge. FIG. 7 includes an illustration of an exemplary cartridge 702 disposed within a test media adapter 710 to form a test medium 700. The cartridge 702 includes a port 704 for applying liquid samples. The cartridge 702 may include reagents or chromatographic media useful in detecting analytes in liquids. In other examples, the cartridge 702 may include dry chemistry, mechanical, electromechanical, or electronic components for performing analyte detection. Results of the detection may be displayed via window 706. For example, a location of a line, a color change, or the appearance of a symbol may be observable through the window 706. In the case of electronic components, light emitting diodes or other electronic indicators may indicate detection of an analyte.

The cartridge 702 may further include identifiers, such as color coding, numerical coding, or bar codes. In one particular embodiment, the cartridge 702 includes an RFID component 708 embedded within the cartridge 702. When placed within a reader module that includes an RFID antenna, the RFID component 708 may provide RFID data that uniquely identifies the cartridge. In one particular embodiment, the RFID data identifies the cartridge type, the specific cartridge, the lot number, expiration dates, and analytes that the cartridge is configured to detect. In another embodiment, the RFID tag component 708 may also be configured to store test results. For example, the component may be provided with test results, the time and date that a test was performed and proximate conditions associated with the test, such as temperature and humidity.

In an alternative embodiment, the component 708 may receive electromagnetic signals useful for generating power. Such power may be used to generate heat or operate electronic or electromechanical devices within the cartridge.

Figure 8:
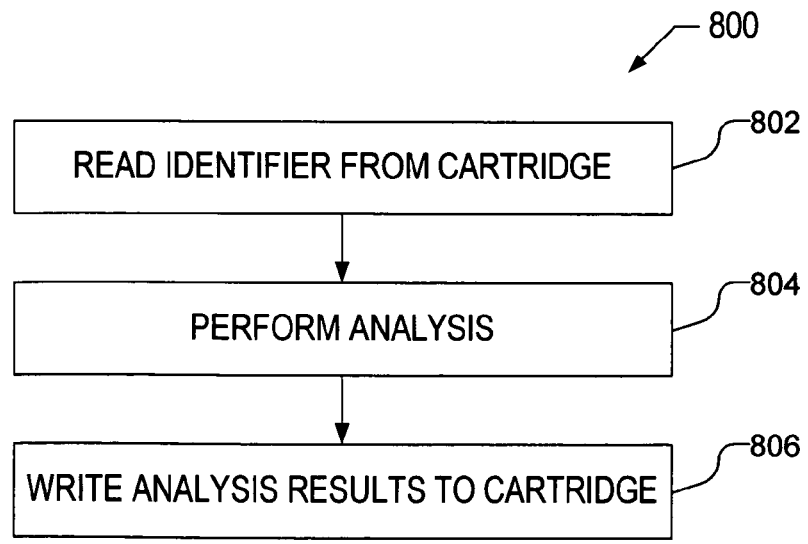
FIG. 8 includes an illustration of an exemplary method for performing analyte detection.

FIG. 8 includes an exemplary method 800 for analyzing a test media, such as a cartridge. For example, an identifier may be read from the cartridge, as illustrated at 802. In one particular embodiment, an RFID tag is accessed from the cartridge. The identifier may be used to determine how to analyze the image of the cartridge, such as to access parameters stored in a database. An image is read and analysis of the image is performed, as illustrated at 804. Once the test results are available, the results may be written to the cartridge, as illustrated at 806. In a particular embodiment, a radio frequency antenna associated with the reader module directs results data to the cartridge for storage. For example, the reader module may send a first radio frequency signal to acquire a RFID from the cartridge and send a second radio frequency signal including data, such as test results, for storage on the cartridge.

Figure 9:
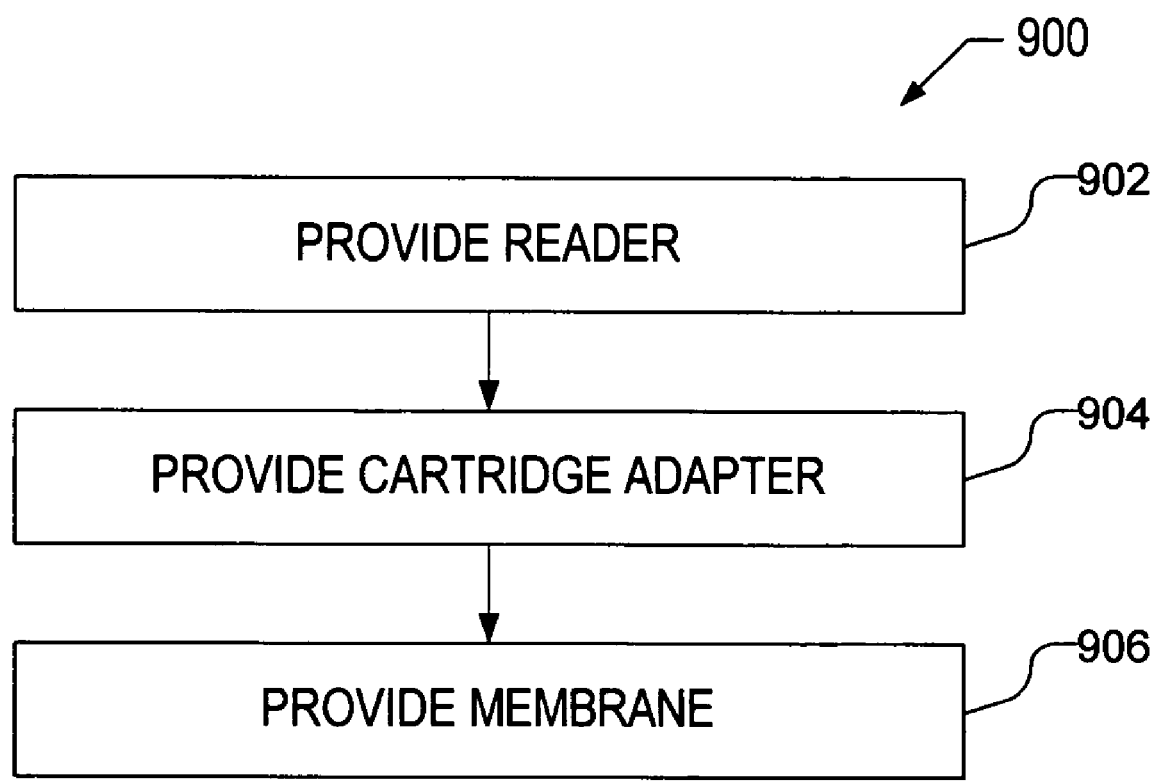
FIG. 9 includes an illustration of an exemplary method for distributing components to perform testing.

The reader, test media adapters, and membranes may be provided to users. Consumed items, such as membranes and test media, may be subsequently provided to consumers who have the test media reader and adapters. In addition, software and analysis parameters associated with analyzing particular test media may be provided to consumers. For example, software and analysis parameters may be provided on a computer readable media, such as an optical media, magnetic media or via networks, to facilitate analysis of test media. For example, FIG. 9 includes an illustration of an exemplary method 900 for distributing reader components to users. The method includes providing a reader, as illustrated at 902. In addition to the reader, software may be provided to the user, such as software for installation on a PDA. The reader may be adapted to receive cartridge adapters. For example, cartridge adapters may be provided for adapting test strips and cartridges for viewing through an optical window associated with the reader module, as illustrated at 904. In addition, membranes having active regions and configured to attach to a window of the reader module may be provided, as illustrated at 906. For example, a stack of membranes having reactive regions viewable through a window of a reader module may be provided to users of the reader module.

Particular embodiments of the above disclosed test media readers, membranes, and cartridges may be used by hazardous materials (HAZMAT) handlers to detect chemical and biological hazards. In another embodiment, the test media readers, membranes, and cartridges are useful in medical facilities for performing tests, such as urine tests, blood tests, and saliva tests. In a further example, embodiments may be used to monitor environmental conditions, such as through in-field testing. In a particular embodiment, such embodiments may be used to detect chemical and biological agents used by terrorists.

The above-disclosed subject matter is to be considered illustrative, and not restrictive, and the appended claims are intended to cover all such modifications, enhancements, and other embodiments, which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A test media reader module comprising:
   a test media adapter configured to receive a test media that provides optical indication of a presence of a first analyte;

a housing configured to couple to the test media adapter, the housing having a barrier configured to separate the test media adapter from an interior of the housing, the barrier including a window having an interior side and an exterior side;

a membrane transparent to a wavelength useful for imaging a particular test media in the test media adapter, the membrane having at least one reactive region responsive to a proximate condition to change at least one optical characteristic of the at least one reactive region, the membrane overlying at least a portion of the exterior side of the window; and an optical imager located proximal to the interior side of the window, wherein the optical imager is operative to capture an image including the particular test media in the test media adapter and the at least one reactive region of the membrane along an optical path extending through the window and the membrane.

2. The test media reader module of claim 1, wherein the housing is configured to receive a handheld electronic device.

3. The test media reader module of claim 1, wherein the membrane is one membrane of a stack of membranes overlying the exterior side of the window.

4. The test media reader module of claim 1, wherein the at least one reactive region of the membrane is transparent to the wavelength prior to exposure to the proximate condition.

5. The test media reader module of claim 1, wherein the at least one optical characteristic of the at least one reactive region includes at least one of a change in color and a change in transmissivity.

6. The test media reader module of claim 1, wherein the proximate condition to change optical characteristics of the at least one reactive region is selected from the a group consisting of humidity, temperature, a concentration of air borne analytes, a concentration of volatile chemicals, and any combination thereof.

7. The test media reader module of claim 1, further comprising an antenna coupled to the housing.

8. The test media reader module of claim 7, wherein the antenna is configured to access a radio frequency identification tag coupled to the particular test media.

9. The test media reader module of claim 7, wherein the antenna is configured to transmit and receive data to and from the particular test media.

10. The test media reader module of claim 1, wherein the at least one reactive region comprises a plurality of reactive regions, wherein two or more of the reactive regions are responsive to different proximate conditions.

11. The test media reader module of claim 1, wherein the membrane includes an identifier, and wherein the captured image includes the identifier of the membrane.

12. The test media reader module of claim 1, wherein the proximate condition to change optical characteristics of the at least one reactive region includes a contact of the at least one reactive region by a second analyte different from the first analyte.

13. The test media reader module of claim 1, further comprising a processing device to analyze the captured image using different test criteria for a first portion of the captured image including the particular test media and for a second portion of the captured image of including the at least one reactive region.

14. A system, comprising:
a housing including a window;
an optical imager located in the housing on a first side of the window;
a membrane positionable on a second side of the window to overlie at least a portion of the window, wherein the membrane includes a transparent region and at least one reactive region responsive to a proximate condition to change optical characteristics of the at least one reactive region;
a test media adapter configured to couple to the housing; and
a test media positionable in the test media adapter such that the membrane is positioned between the window and the test media when the membrane is positioned on the second side of the window and the test media adapter is coupled to the housing, wherein the test media provides an optical indication of a presence of a first analyte;
wherein the optical imager is configured to capture an image of the test media and the at least one reactive region of the membrane.

15. The system of claim 14, wherein the test media comprises a display window, and wherein an indication of the presence of the first analyte is shown in the display window.

16. The system of claim 14, wherein the test media comprises a port to accept liquid samples.

17. The system of claim 14, wherein the test media comprises a radio frequency identification component.

* * * * *